United States Patent [19]

Foster et al.

[11] 4,192,438

[45] Mar. 11, 1980

[54] DEVICE FOR DELIVERING RADIOACTIVE GAS FROM A SEALED VIAL

[75] Inventors: Edward H. Foster; James M. Reiss, both of Center Moriches, N.Y.

[73] Assignee: Atomic Products Corporation, Center Moriches, N.Y.

[21] Appl. No.: 909,504

[22] Filed: May 25, 1978

[51] Int. Cl.$^2$ .......................... A61B 6/00; B67B 7/24
[52] U.S. Cl. ........................................ 222/5; 128/654; 222/400.7
[58] Field of Search ............... 222/5, 400.7; 128/2 A, 128/1.1, 1.2; 250/432 PD

[56] References Cited

U.S. PATENT DOCUMENTS

| | | | |
|---|---|---|---|
| 2,016,113 | 10/1935 | Lambert et al. | 222/5 |
| 2,955,729 | 10/1960 | Kish | 222/400.7 |
| 3,848,773 | 11/1974 | Adler et al. | 222/5 X |
| 4,045,525 | 8/1977 | Huggins | 222/400.7 X |

FOREIGN PATENT DOCUMENTS 1293052  4/1969  Fed. Rep. of Germany ........ 222/400.7

*Primary Examiner*—John P. Shannon
*Attorney, Agent, or Firm*—Charles E. Temko

[57] ABSTRACT

A gun type device for removing radioactive gas from a sealed hypodermic type vial. The device includes a sealable recess including a pair of concentric hollow needles which penetrate the vial upon the closing of the chamber with a vial still remaining within a lead shielded container which then forms a part of the sealed chamber. An inlet port under control of a push button valve conducts an inert gas under compression through one of said needles to displace and mix with the radioactive gas and force the same through the other of said needles to an outlet port controlled by a second valve.

3 Claims, 6 Drawing Figures

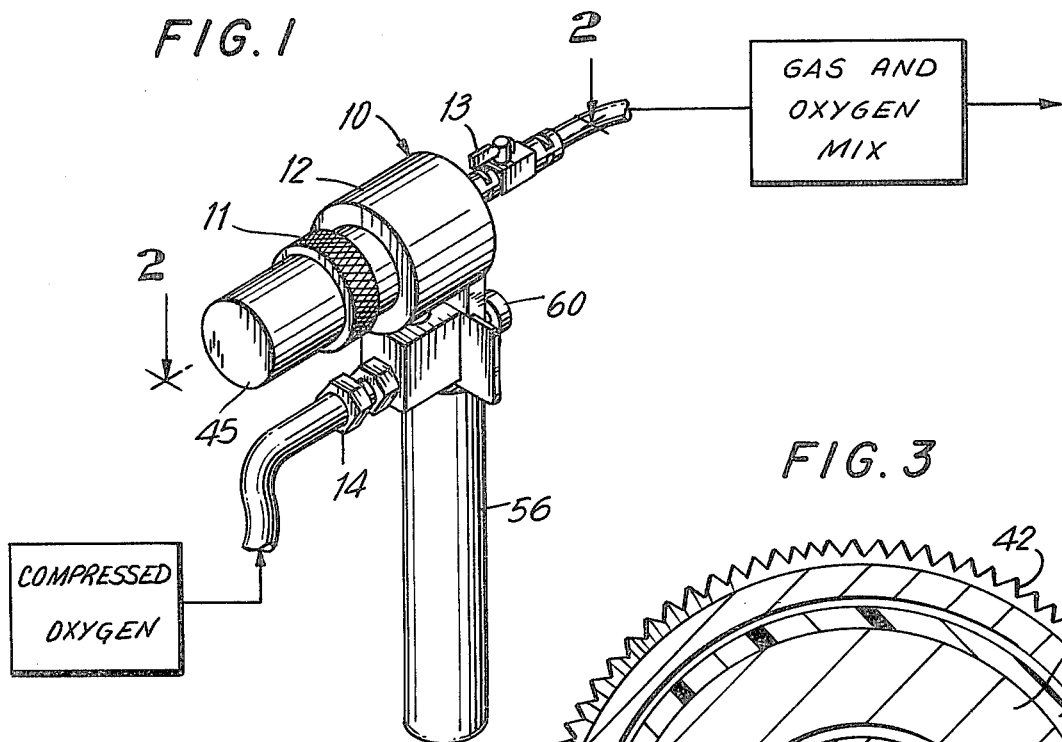
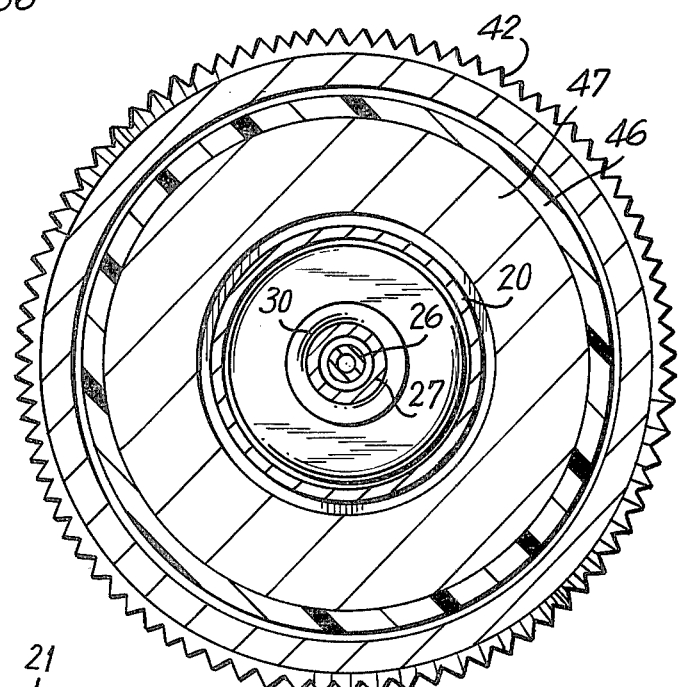
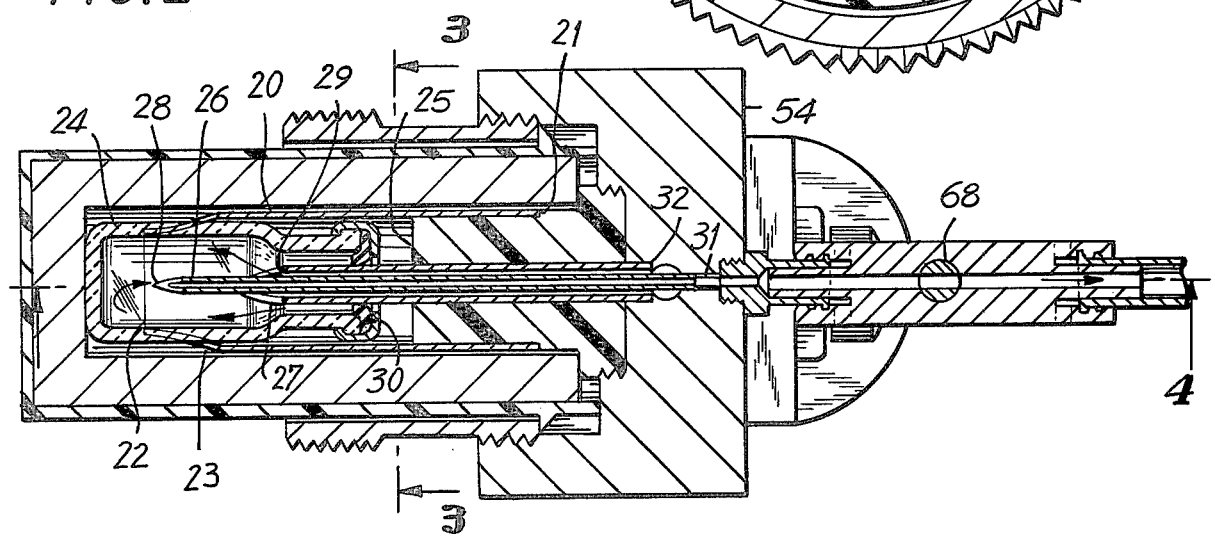

DEVICE FOR DELIVERING RADIOACTIVE GAS FROM A SEALED VIAL

BACKGROUND OF THE INVENTION

This invention relates generally to the field of nuclear medicine, and more particularly to an improved device for removing a radioactive gas (Xenon) from a hypodermic type vial to be conducted to a gas delivery unit of known type used for conducting regional ventilation studies upon a patient. Such studies are well-known in the medical art, and a description of the same is outside the scope of the present disclosure.

In performing such studies, it is common to use individual doses of Xenon gas for each patient, which are supplied to a disposable mouthpiece section forming part of the Xenon delivery unit. The quantity of gas required for an individual study is relatively small, and is most conveniently packed in a small glass vial under relatively low pressure, the vial being sealed by a hypodermic type synthetic rubber membrane. The gas can be removed using a conventional hypodermic needle, and transferred to a breathing bag forming part of the delivery unit, or directly to the face mask used by the patient. This technique has not proved to be entirely satisfactory, for the reason that hypodermic needles are essentially designed to accommodate liquids rather than gases, and are subject to leakage. Further, unless a shield is used, the radioactive gas in the hypodermic syringe subjects the technician to repeated exposure. It is also known in the art to use a rubber bulb type device for injecting air into the vial to force the contents outwardly thereof, but this is essentially a hand operation, requiring repeated impulses to the rubber bulb, and, again, its use has not been entirely satisfactory.

SUMMARY OF THE INVENTION

Briefly stated, the invention contemplates a gun type device having means for completely enclosing the vial during delivery, so that it is completely surrounded by shielding material. Since a Xenon delivery system normally includes a source of gas (oxygen) under pressure, this source is used to provide a gas under pressure, which is inert relative to the Xenon gas, which may be injected into the vial to rapidly displace the Xenon gas in a matter of a few seconds. The device includes means forming a receptor for the vial while still disposed in its protective lead shielding, such that a pair of concentric needles penetrate the membrane, while a threaded bushing engages the lead shielded container to form a completely enclosed recess. The needles communicate with inlet and outlet ports in a housing, and the compressed oxygen is supplied through a manually controlled valve into the inlet port for such displacement. The outlet port communicates with another of the needles, the outlet port including a petcock which prevents the loss of the radioactive gas until required. When the device is opened for replacement with a fresh vial, all of the radioactive gas has been removed, and the exhausted vial may be manually removed from engagement with the needles with complete safety to the technician.

BRIEF DESCRIPTION OF THE DRAWING

In the drawing, to which reference will be made in the specification, similar reference characters have been employed to designate corresponding parts throughout the several views.

FIG. 1 is a fragmentary view in perspective of an embodiment of the invention.

FIG. 2 is a horizontal enlarged fragmentary sectional view thereof, as seen from the plane 2—2 in FIG. 1.

FIG. 3 is a transverse sectional view thereof as seen from the plane 3—3 in FIG. 2.

DETAILED DESCRIPTION OF THE DISCLOSED EMBODIMENT

Figure 4:
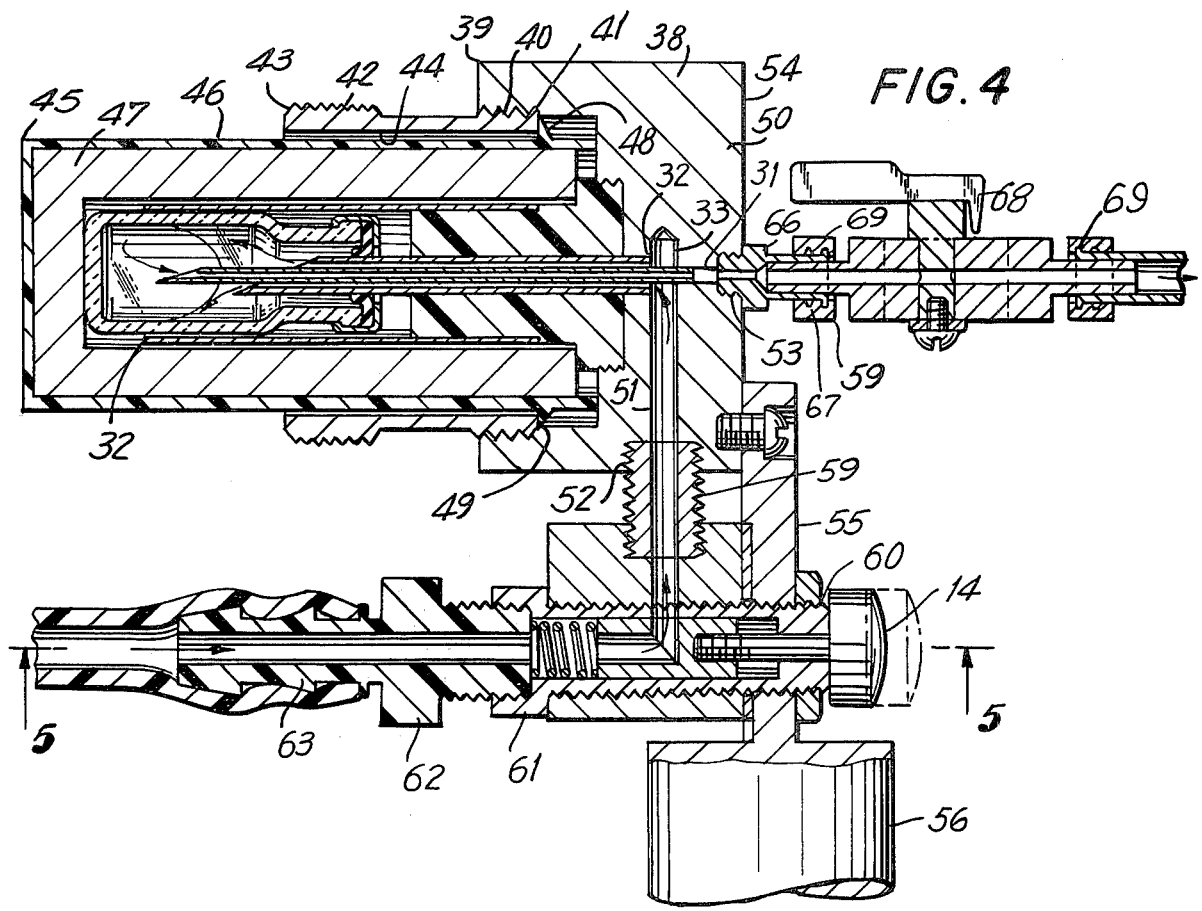
FIG. 4 is a fragmentary vertical sectional view as seen from the plane 4—4 in FIG. 2.
Figure 5:
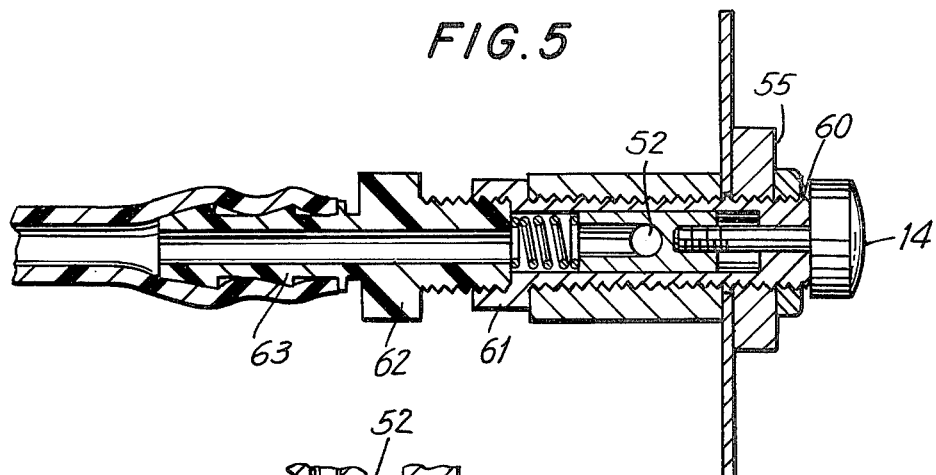
FIG. 5 is a fragmentary horizontal sectional view as seen from the plane 5—5 in FIG. 4.
Figure 6:
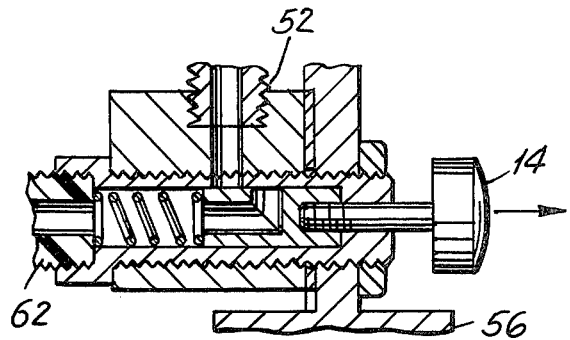
FIG. 6 is a fragmentary sectional view corresponding to that seen in FIG. 4, and showing certain of the component parts in altered relative condition.

In accordance with the invention, the device, generally indicated by reference character 10, comprises broadly: a vial receiving element 11, a sealable housing element 12, compressed gas outlet means 13 and compressed gas inlet means 14. The vial receiving element 11 includes a cylindrical tube 20, an upper end 21 of which engages the housing element 12. A lower end 22 is provided with a pair of identations 23 to permit manual removal of a vial 24. A sealing plug 25 supports a pair of concentric inner and outer needles 26 and 27, respectively, the lower ends 28 and 29 thereof being adapted to penetrate the synthetic rubber plug or membrane 30 of the vial 24 in well-known manner. The upper ends 31 and 32 of the needles 26 and 27 extend through the gasket 25 into an enclosed chamber 33 in the housing element 12.

The housing element 12 includes a cylindrical wall 38, the lower threaded flange 39 of which is provided with internal threads 40 to accommodate the threaded end 41 of a cylindrical bushing 42. The lower end 43 of the bushing is suitably knurled to facilitate manual engagement. The through bore 44 is of dimension to accommodate the cylindrical body 45 of a lead-lined container of known type which includes an outer synthetic resinous member 46 having a lead lining 47 which encloses the vial 24. The outer surface of the member 46 includes annular bead 48 which engages the upper surface 49 of the bushing 42.

Thus, to engage a vial 24 with the device, it is necessary only to remove the cover (not shown) of the body 45, drop the body 45 into engagement with the bushing 42, and proceed to engage the bushing with the threads 40 on the lower end 39. Before engagement of the threads, the needles 26-27 will penetrate the plug 30, and shortly thereafter the tightening of the bushing will completely enclose the recess formed by the lower end 39.

The upper portion 50 of the element 12 includes an enclosed chamber 51 having a threaded inlet port 52 and a threaded outlet port 53, the ports communicating each with the upper ends of one of the needles 26 and 27. Secured to an uppermost horizontal surface 54 is an extension 55 of a manually engageable handle 56.

The port 52 is engaged by a threaded tube 59 communicating with a push button valve assembly 60 having a housing 61 and a downwardly extending inlet 62 having a connection 63 for communicating with a source (not shown) of compressed oxygen.

Also extending outwardly from the surface 54 is a threaded tube 66 having a quick release fitting 67 and a stopcock valve 68 having corresponding fittings 69 on both ends thereof. The outer most fitting 69 is connected to a suitable fitting and conduit (not shown) communicating with the Xenon delivery unit.

In operation, the valve 68 is opened just prior to opening the valve assembly 60, so that no loss of gas occurs prior to emptying of the vial under pressure.

I wish it to be understood that I do not consider the invention limited to the precise details of structure shown and set forth in this specification, for obvious modifications will occur to those skilled in the art to which the invention pertains.

I claim:

1. A device for delivering radioactive gas from a sealed vial to a gas delivery unit for performing regional ventilation studies and the like, comprising: a housing element defining an enclosed chamber and a threaded flange adjacent said chamber and defining a recess; inlet and outlet ports communicating with said enclosed chamber; a pair of concentrically disposed hollow needles extending from said enclosed chamber into said recess, one end of each of said needles disposed in said chamber communicating with one of said inlet and outlet ports; a vial receiving element positioned within said recess, and disposed in the area of opposite ends of said concentric needles; a threaded cylindrical bushing selectively engageable with said threaded flange and having means engaging a protective shielded container of a vial after the removal of a cover of said container, said engagements positioning a vial disposed within said container opposite said needles for the simultaneous penetration thereof; and coupling means connecting with said inlet port including a manually operable valve for supplying an inert gas under pressure through one of said needles into said vial; whereby upon the engagement of a vial upon said needles, and the opening of said manually operable valve, gas under pressure may be supplied through one of said needles to displace gas within said vial and force the same through the other of said needles and through said outlet port.

2. A device as set forth in claim 1, further comprising a second manually operable valve in series with said outlet port for preventing loss of gas upon the penetration of a via prior to the introduction of gas under pressure through said inlet port.

3. A device in accordance with claim 1, further characterized in said vial receiving element including a cylindrical tube adapted to surround an engaged vial inwardly of said shielded container.

* * * * *